United States Patent
Sato

(10) Patent No.: US 12,370,036 B2
(45) Date of Patent: Jul. 29, 2025

(54) METHOD OF CONTROLLING SYMPTOMS RELATING TO COVID-19

(71) Applicant: Takahiro Sato, Tokyo (JP)

(72) Inventor: Takahiro Sato, Tokyo (JP)

( * ) Notice: Subject to any disclaimer, the term of this patent is extended or adjusted under 35 U.S.C. 154(b) by 355 days.

(21) Appl. No.: 18/095,409

(22) Filed: Jan. 10, 2023

(65) Prior Publication Data

US 2024/0225811 A1 Jul. 11, 2024

(51) Int. Cl.
*A61F 2/01* (2006.01)

(52) U.S. Cl.
CPC ...................... *A61F 2/01* (2013.01)

(58) Field of Classification Search
CPC .............. A61F 2/0105; A61F 2002/016; A61F 2002/018; A61F 2/011; A61F 2/01; A61F 2/0103; A61F 2/012; A61F 2/00; A61F 2/0108; A61F 2/856; A61F 2/86; A61F 2/94; A61F 2/92; A61F 2/88; A61F 2/91; A61F 2/90; A61F 2/89
See application file for complete search history.

(56) References Cited

U.S. PATENT DOCUMENTS

| | | | |
|---|---|---|---|
| 2004/0059373 A1* | 3/2004 | Shapiro | A61F 2/0105 606/200 |
| 2005/0055046 A1* | 3/2005 | McGuckin | A61F 2/01 606/200 |
| 2005/0288703 A1* | 12/2005 | Beyer | A61F 2/0103 606/200 |
| 2012/0130468 A1* | 5/2012 | Khosravi | A61M 25/104 623/1.11 |

OTHER PUBLICATIONS

Masunaga—Novel therapeutic thin endoscope facilitates endoscopic submucosal dissection for cervical esophageal cancer involving the pharyngoesophageal junction (Year: 2023).*
Cheng—COVID-19 related thrombosis: A mini-review (Year: 2022).*
Eleftheriadis—Endoprosthesis implantation at the pharyngoesophageal level: Problems, limitations and challenges (Year: 2005).*
Sato, et al., "Palisading longitudinal esophagus vessels at esophagogastric junction", Hepatogastroenterology. Mar.-Apr. 2008; 55(82-83): 305-7.
Sato, et al., "Significance of Palisading Longitudinal Esophagus Vessels: Identification of the True Esophagogastric Junction Has Histopathological and Oncological Considerations", Dig Dis Sci. Nov. 2010; 55(11): 3095-101.

* cited by examiner

*Primary Examiner* — Eduardo C Robert
(74) *Attorney, Agent, or Firm* — Holtz, Holtz & Volek PC

(57) ABSTRACT

A method of controlling symptoms relating to COVID-19 is provided. A filter is placed in a vein of a patient. The filter is placed between a heart and a palisading longitudinal esophageal vessel (PLEV) at a pharyngoesophageal junction (PEJ).

11 Claims, 5 Drawing Sheets

METHOD OF CONTROLLING SYMPTOMS RELATING TO COVID-19

BACKGROUND OF THE INVENTION

Field of the Invention

The present invention relates to a method of controlling symptoms relating to COVID-19, in particular to an operation to prevent aggravation of COVID-19.

Description of the Related Art

Rapid progression to death as well as high infectious capacity are fundamental dangers of COVID-19. Common treatment options include administration of an antivirus agent such as remdesivir and molnupiravir, an antibody such as sotrovimab, casirivimab and imdevimab, and a steroidal agent such as dexamethasone. However, in view of a rapidly changing nature of COVID-19, more treatment options are needed.

SUMMARY OF THE INVENTION

According to an embodiment of the present invention, a method of controlling symptoms relating to COVID-19 comprises placing a filter in a vein of a patient, wherein the filter is placed between a heart and a palisading longitudinal esophageal vessel (PLEV) at a pharyngoesophageal junction (PEJ).

According to another embodiment of the present invention, a method of controlling symptoms relating to COVID-19 comprises resecting a PLEV at a PEJ.

According to an embodiment of the present invention, a method of controlling symptoms relating to COVID-19 comprises covering a surface of a PEJ.

Further features of the present invention will become apparent from the following description of exemplary embodiments with reference to the attached drawings.

DESCRIPTION OF THE EMBODIMENTS

Figure 1:
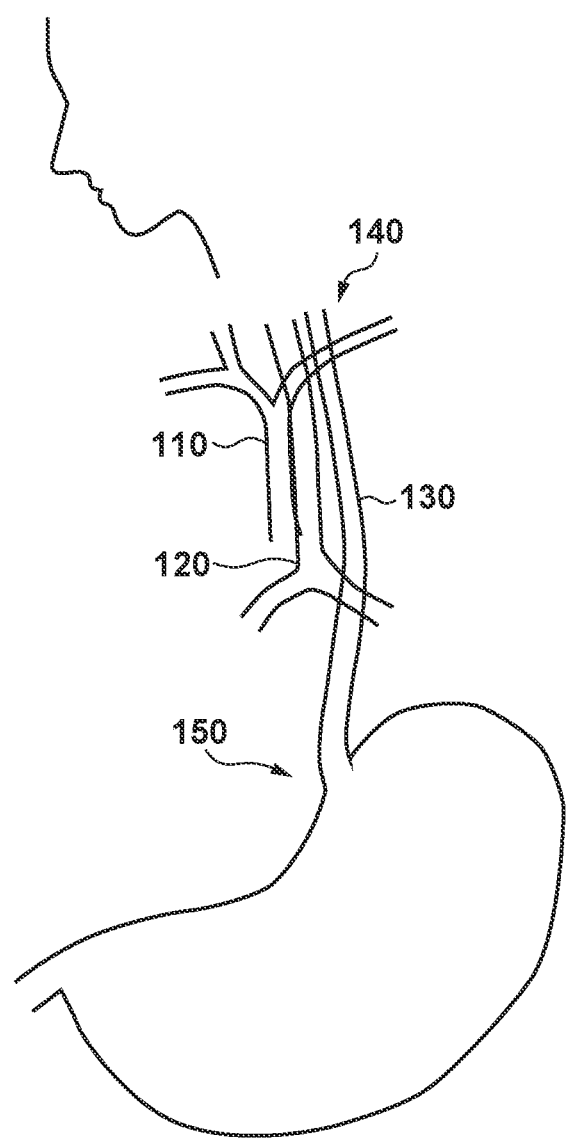
FIG. 1 is a schematic representation of a mediastinum.

Hereinafter, embodiments will be described in detail with reference to the attached drawings. Note that the following embodiments are not intended to limit the scope of the claimed invention, and limitation is not made an invention that requires all combinations of features described in the embodiments. Two or more of the multiple features described in the embodiments may be combined as appropriate. Furthermore, the same reference numerals are given to the same or similar configurations, and redundant description thereof is omitted.

The inventor focused on a relationship between aggravation of COVID-19 and palisading longitudinal esophageal vessels (PLEVs). The inventor previously reported that PLEVs exist at the surface of the esophagus at high density (Sato T, Kato Y, Matsuura M, and Gagner M. "Significance of Palisading Longitudinal Esophagus Vessels: Identification of the True Esophagogastric Junction Has Histopathological and Oncological Considerations", Dig Dis Sci. 2010 November; 55(11): 3095-101, Sato T and Kato Y. "Palisading longitudinal esophagus vessels at esophago-gastric junction", Hepatogastroenterology. 2008 March-April; 55(82-83): 305-7.).

Figure 2:
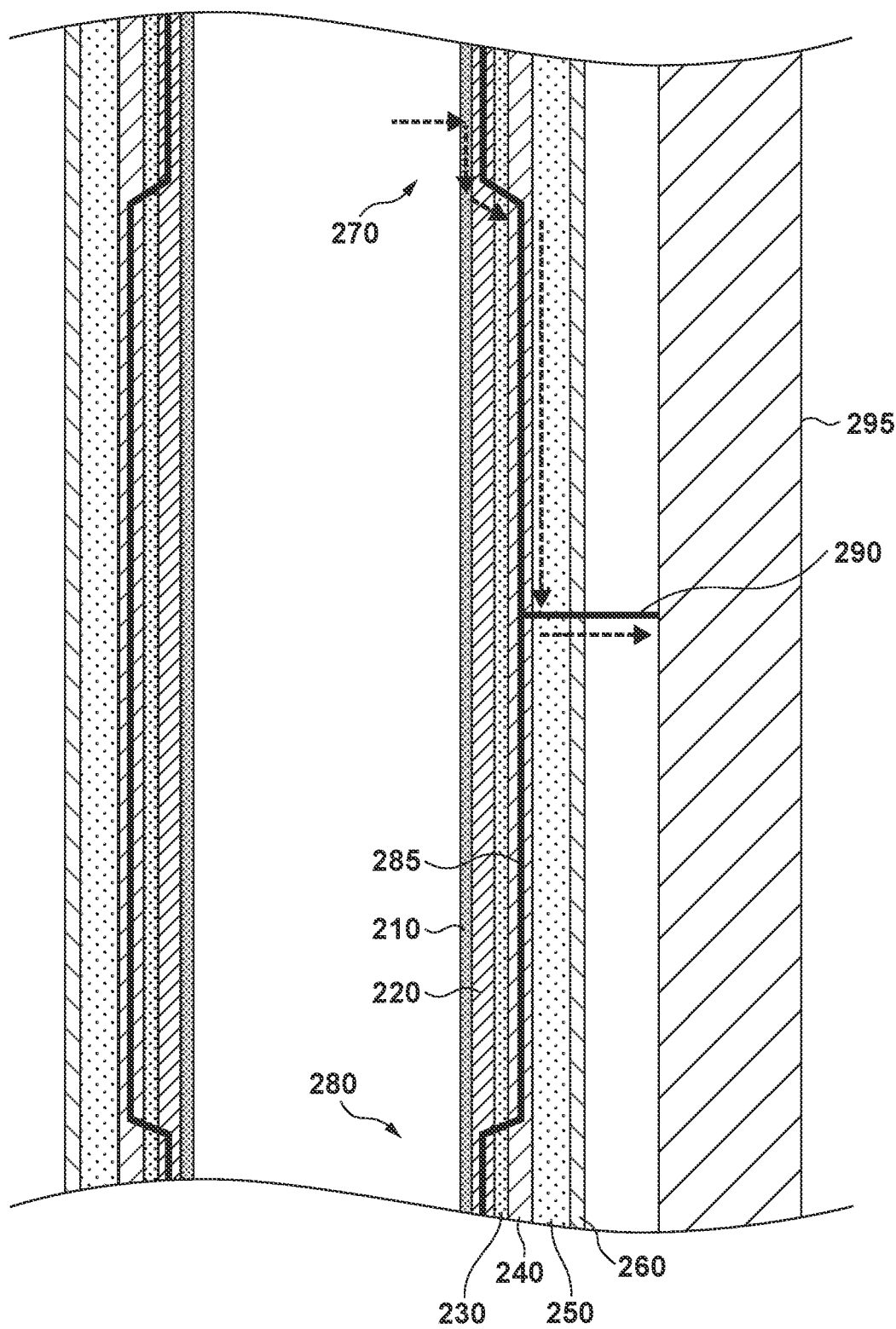
FIG. 2 is a schematic representation of a longitudinal section of an esophagus.

Anatomically, a superior vena cava (SVC) 110, a trachea 120, and an esophagus 130 exist in the same narrow space of a mediastinum, as illustrated in FIG. 1. The PLEVs are recognized in a pharyngoesophageal junction (PEJ) 140 and an esophagogastric junction (EGJ) 150. Also, a vascular density in the PLEVs is high. The PLEVs originate in a portal vein. Portal veins do not have valve structures, at all. FIG. 2 is a schematic representation of a longitudinal section of an esophagus. A wall of the esophagus has an epithelium 210, a lamina propria 220, a muscularis mucosae 230, a submucosa 240, a muscle layer 250, and an adventitia 260. The PLEVs at the PEJ 270 (as well as at the EGJ 280) can be found in the lamina propria 220 and penetrate into a submucosa 240 at the PEJ 270. The blood stream from the PLEV flows through an esophagus vein 285, into an azygous vein 290, or right and left superior intercostal veins, and finally into the SVC 295, as indicated by the dotted arrow. This route of the blood flow also does not have a valve structure, at all.

SARS-CoV-2, which causes COVID-19, is likely to infect endothelial cells in which ACE-2 are positive and abundant. PLEVs are easily invaded by micro-organisms due to their superficiality. Thus, a PEJ is anatomically sensitive to COVID-19 infection. In particular, in a senile patient, who has swallowing difficulty, transition time in the PEJ area is longer and therefore there is an increased invasion risk in this patient. Furthermore, a mucosal barrier of the PEJ will be damaged by the patient vomiting, acute elevation of intra-esophageal pressure, reflux esophagitis, strong squeezing of the swallowing muscles, etc.

Once micro-organisms enter these vessels, they can proceed into an SVC, the right atrium, and the right ventricle, and then into pulmonary arteries, pulmonary capillaries, and alveolar arteries. These small caliber vessels are easily obstructed due to a thrombus or inflammation. The resulting phenomenon can be recognized as an interstitial pneumonia on computed tomography (CT). At an initial stage of COVID-19, an abnormal shadow will develop at peripheral regions of the lung on CT. This may be an important pathway by which the SARS-Cov-2 infection progresses into a life-threatening condition, i.e., pneumonia, a pulmonary thrombus, and so on.

Usually, a deep venous thrombus (DVT) is formed in the lower extremities. However, in the PLEV associated pathway, a thrombus is formed in the SVC or the right atrium. Therefore, the first attack by micro-organisms should be blocked, or a thrombus should be blocked before the thrombus enters the heart. In this way, a rapid progression of COVID-19 and a life-threatening condition resulting therefrom can be prevented in the route from the PLEV at the PEJ, through the SVC, to the heart.

According to an embodiment, a method of controlling symptoms relating to COVID-19 comprises placing a filter in a vein of a patient. The filter is placed between the heart and a PLEV at a PEJ. In order to deal with a smaller thrombus, it is possible to use a heparin for thrombus solution. However, in order to deal with a larger thrombus, thrombus harvesting or filtering through a blood access may be needed. The filter placed between the heart and the PLEV at the PEJ can capture a thrombus which originates from the PLEV at the PEJ and prevent the thrombus from entering the heart and the lung.

Figure 3:
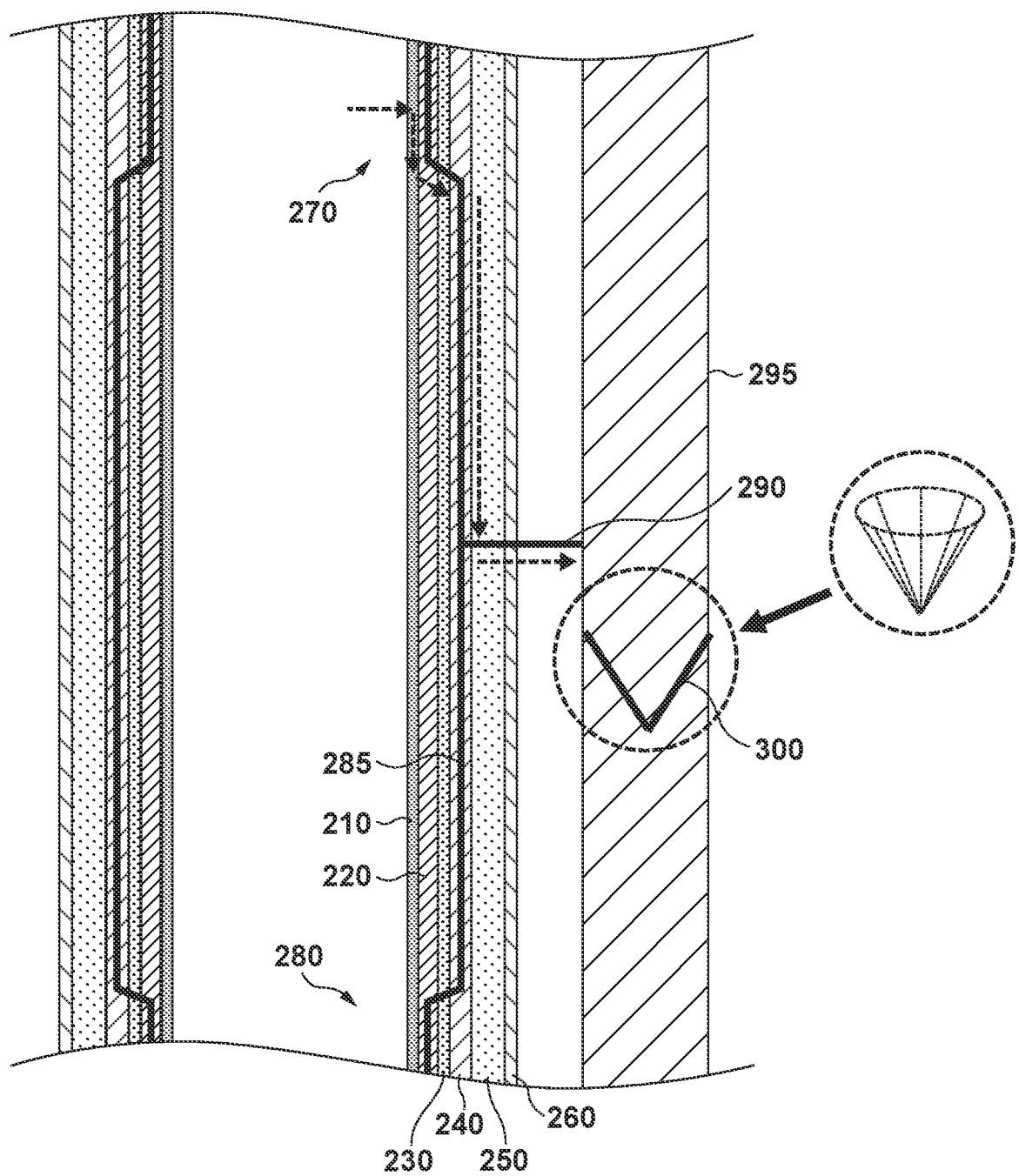
FIG. 3 is a schematic representation of placement of a filter in an SVC.

The filter 300 may be placed in an SVC, as illustrated in FIG. 3. The filter placed in the SVC is effective in capturing a thrombus originating from the PLEV at the PEJ, while it is relatively easy to access the SVC percutaneously. However, the filter may be placed in a vein at another position between the heart and the PLEV at the PEJ.

The filter may be a thrombus trapping filter. An inferior vena cava filter for trapping a thrombus may be used for this purpose. The filter may be a temporary filter, so that the filter can be removed after recovery from COVID-19. In an embodiment, the filter is removed after recovery from COVID-19. On the other hand, the filter may be a permanent filter for permanent placement, which may be beneficial to a patient with a very high risk of aggravation.

In order to place the filter in the vein, a percutaneous transcatheter approach can be applied. This approach may include punctuation at a basilic vein, a subclavian vein, or an internal jugular vein, advancement of a guide wire and a catheter from the point of punctuation to the SVC, and introduction of the filter to the SVC along with the guide wire.

As described above, the PLEV at the PEJ is a target of invasion by SARS-CoV-2. According to an embodiment, a method of controlling symptoms relating to COVID-19 comprises preventing SARS-CoV-2 from entering the PLEV at the PEJ. This prevention is effective as prophylaxis against a life-threatening process associated with COVID-19. The prevention of SARS-CoV-2 from entering the PLEV at the PEJ may be used alone and may be used in combination with placement of the filter as described above.

Figure 4:
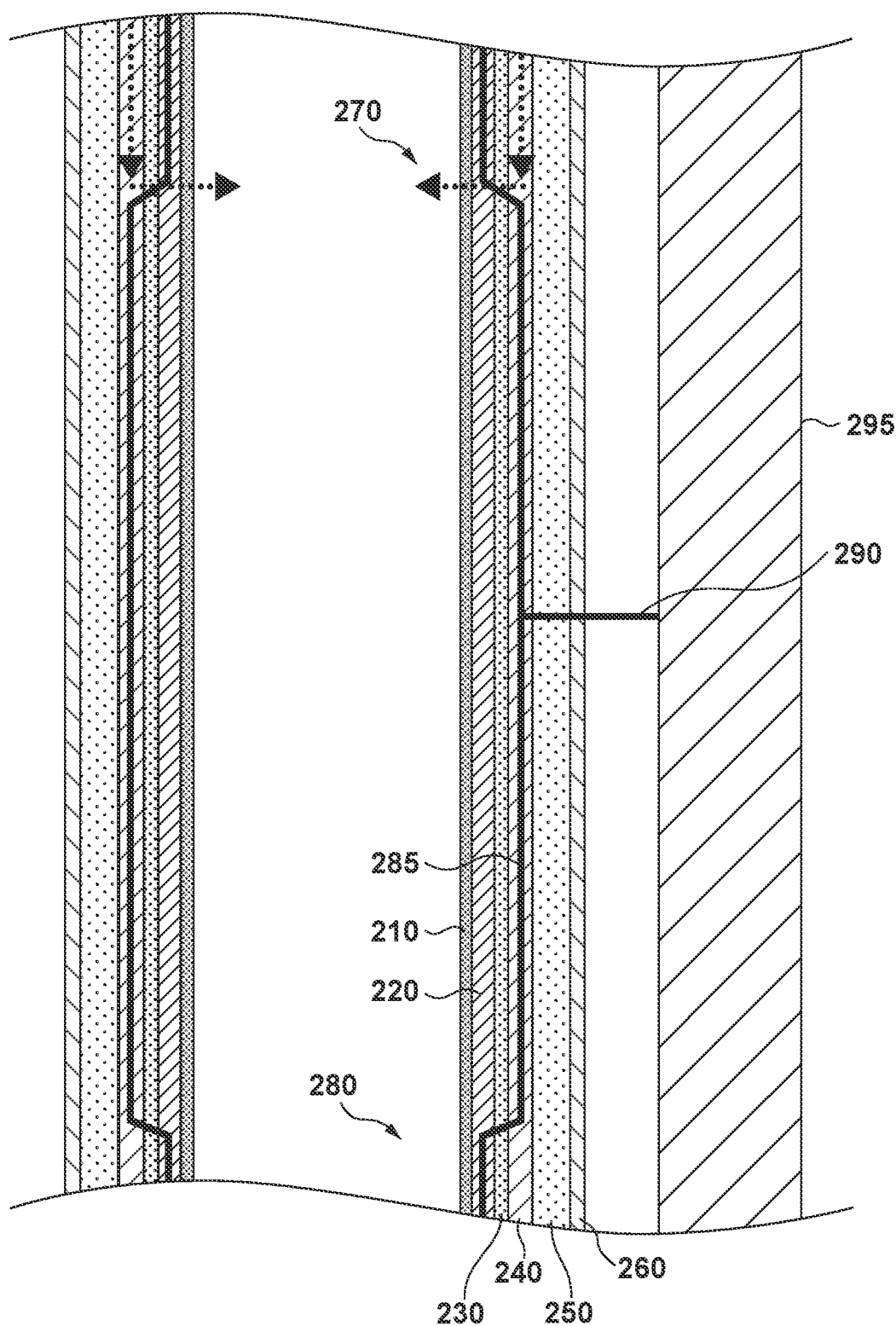
FIG. 4 is a schematic representation of resection of a PLEV at a PEJ.

In order to prevent SARS-CoV-2 from entering the PLEV at the PEJ, the method of controlling symptoms relating to COVID-19 may comprise resecting the PLEV at the PEJ. The PLEV at the PEJ may be entirely removed by resection, while the PLEV at the PEJ may be partially resected to restrict the target of invasion by SARS-Cov-2. In an embodiment, a mucosa (including an epithelium, a lamina propria, and a muscularis mucosae) and a submucosa at the PEJ may be resected. The resection may be performed endoscopically, for example, by endoscopic submucosal dissection (ESD). For example, the PLEV at the PEJ can be dissected along the dotted arrow illustrated in FIG. 4. This resection may also be effective in reducing a thrombus originating from the PLEV at the PEJ.

Figure 5:
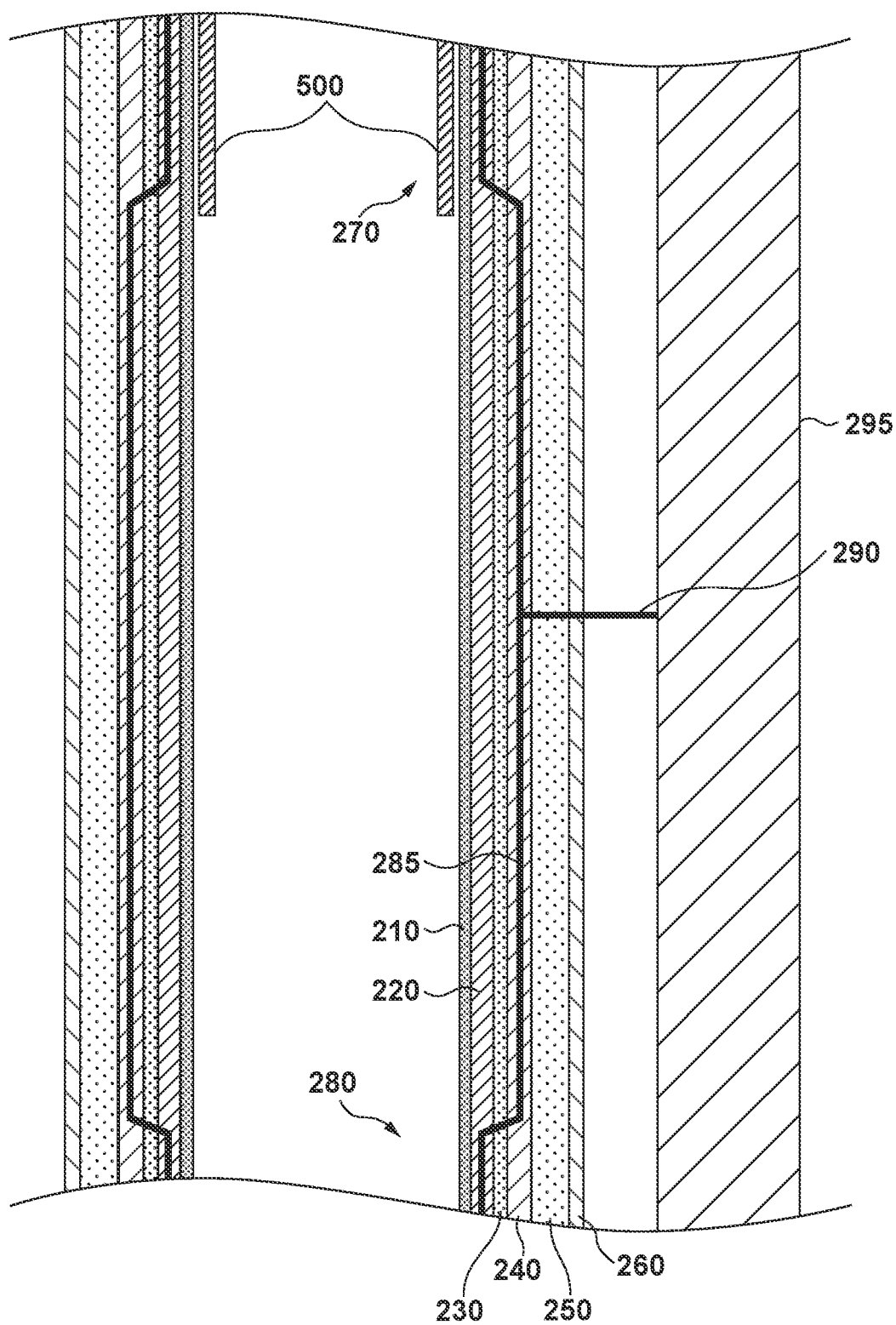
FIG. 5 is a schematic representation of cover of a PEJ.

In another embodiment, the method of controlling symptoms relating to COVID-19 may comprise covering a surface of the PEJ with a cover 500 in order to prevent SARS-CoV-2 from entering the PLEV at the PEJ, as illustrated in FIG. 5. For example, the cover 500 may be a sheet, a prosthesis, or a stent and may be applied to the surface of the PEJ to cover the PEJ. The PEJ may be entirely covered, while the PEJ may be partially covered to restrict the target of invasion by SARS-Cov-2. This cover of the PEJ may be applied on its own and may be applied in combination with the resection of the PLEV at the PEJ.

The sheet for covering the PEJ may be made of colloid gel or fibrin glues. The sheet may contain medicine. The prosthesis may be a short segment covered prosthesis. The prosthesis or the stent may have a cylindrical shape to fit with the PEJ. The prosthesis or the stent may be made of rubber or silicone.

The patient may suffer from COVID-19. The control of symptoms relating to COVID-19 in an embodiment includes prevention of aggravation of symptoms relating to COVID-19 in the patient. In particular, the control of symptoms relating to COVID-19 may include preventing the patient from developing pneumonia. On the other hand, the patient may be a healthy patient, or a healthy patient with a high risk of aggravation of COVID-19 when infected such as an elderly patient. In this case, a method according to an embodiment, i.e., placing a filter in a vein of a patient and/or preventing SARS-CoV-2 from entering the PLEV at the PEJ, can be performed for prophylactic purposes prior to SARS-CoV-2 infection.

The invention is not limited to the foregoing embodiments, and various variations/changes are possible within the spirit of the invention.

What is claimed is:

1. A method of controlling symptoms relating to COVID-19, comprising:
   placing a filter in a vein of a patient, wherein the filter is placed between a heart and a palisading longitudinal esophageal vessel (PLEV) at a pharyngoesophageal junction (PEJ); and
   resecting the PLEV at the PEJ.

2. The method according to claim 1, wherein the filter is placed in a superior vena cava.

3. The method according to claim 1, wherein the filter is a thrombus trapping filter.

4. The method according to claim 1, wherein the filter is placed by a percutaneous transcatheter approach.

5. The method according to claim 1, further comprising removing the filter after recovery from COVID-19.

6. The method according to claim 1, further comprising preventing SARS-CoV-2 from entering the PLEV at the PEJ.

7. The method according to claim 1, wherein the PLEV is resected by endoscopic submucosal dissection (ESD).

8. The method according to claim 1, further comprising covering a surface of the PEJ.

9. The method according to claim 1, further comprising placing a sheet, a prosthesis, or a stent to cover the surface of the PEJ.

10. The method according to claim 1, wherein the method prevents aggravation of symptoms relating to COVID-19.

11. The method according to claim 1, wherein the patient is suffering from COVID-19, and the method prevents the patient from developing pneumonia.

* * * * *